US009554788B1

(12) United States Patent
Redler

(10) Patent No.: US 9,554,788 B1
(45) Date of Patent: Jan. 31, 2017

(54) METHODS AND APPARATUS FOR PERFORMING ARTHROSCOPIC SURGERY

(76) Inventor: Michael R. Redler, Fairfield, CT (US)

( * ) Notice: Subject to any disclaimer, the term of this patent is extended or adjusted under 35 U.S.C. 154(b) by 2593 days.

(21) Appl. No.: 11/202,519

(22) Filed: Aug. 12, 2005

(51) Int. Cl.
  A61M 25/06 (2006.01)
  A61B 17/02 (2006.01)

(52) U.S. Cl.
  CPC .................. *A61B 17/0218* (2013.01)

(58) Field of Classification Search
  CPC ............ A61M 29/00; A61B 2017/1205; A61B 17/12172
  USPC .................................................. 606/191, 192
  See application file for complete search history.

(56) References Cited

U.S. PATENT DOCUMENTS

| | | | |
|---|---|---|---|
| 5,217,441 A | | 6/1993 | Shichman |
| 5,331,975 A * | | 7/1994 | Bonutti .......................... 128/898 |
| 5,431,173 A * | | 7/1995 | Chin et al. .................... 128/898 |
| 5,445,615 A | | 8/1995 | Yoon |
| RE35,523 E * | | 6/1997 | Berger .......................... 128/898 |
| 5,697,946 A | | 12/1997 | Hopper |
| 5,779,697 A * | | 7/1998 | Glowa et al. ................. 606/185 |
| 5,836,913 A * | | 11/1998 | Orth et al. ..................... 604/107 |
| 5,913,870 A * | | 6/1999 | DeFonzo et al. ............. 606/190 |
| 6,358,266 B1 * | | 3/2002 | Bonutti .......................... 606/190 |
| 6,524,283 B1 * | | 2/2003 | Hopper et al. ................ 604/264 |
| 7,104,986 B2 * | | 9/2006 | Hovda et al. ................... 606/32 |
| 7,294,136 B2 * | | 11/2007 | Dubrul et al. ................ 606/185 |
| 2004/0082915 A1 * | | 4/2004 | Kadan ...................... 604/164.04 |
| 2005/0165432 A1 | | 7/2005 | Heinrich |
| 2005/0203342 A1 * | | 9/2005 | Kucklick et al. ............. 600/156 |
| 2008/0097606 A1 * | | 4/2008 | Cragg et al. ............... 623/14.12 |

* cited by examiner

*Primary Examiner* — Julie A Szpira
(74) *Attorney, Agent, or Firm* — Mannava & Kang, P.C.; Carol L. Bunner

(57) ABSTRACT

A method and apparatus are disclosed for securing an arthroscopic cannula in place during arthroscopic surgery. The method and apparatus seal the arthroscopic incision to mitigate leakage of fluid from the joint and seepage of the fluid into surrounding tissue. Reducing leakage of fluid during surgery reduces consumption of saline to insufflate the joint, and improves safety in the operating room by reducing accumulation of fluid on the operating room floor. Reducing leakage and tamping the incision also reduces the likelihood of expulsion of the cannula under pressure from the joint. Reducing seepage of fluid into surrounding tissue also reduces stiffening of the joint during surgery which can interfere with manipulation of the joint and instruments to desired positions during surgery. Reducing seepage of fluid into surrounding tissue also reduces the likelihood of complications or extenuating circumstances during surgery due to migration of fluid through expulsion of the cannula by reducing expansion of surrounding soft tissue during manipulation of instruments and the cannula during surgery, and improves patient recovery.

3 Claims, 5 Drawing Sheets

METHODS AND APPARATUS FOR PERFORMING ARTHROSCOPIC SURGERY

TECHNICAL FIELD

The present disclosure relates to arthroscopic surgery, and more particularly to reducing fluid leakage and cannula displacement during arthroscopic surgery.

BACKGROUND

Arthroscopy is the performance of a surgical procedure within naturally occurring joints through a cannula. The procedure may be simple observation and inspection of tissue structures within the joint, or may involve performing surgical steps through the cannula inserted through soft tissue into the joint capsule. Arthroscopic surgery has become routine and is increasingly being adopted for performing surgery within the human knee and shoulder and is being explored and may be adopted for use in other joints such as the elbow, ankle, wrist, etc. By way of example only, arthroscopy is commonly used in connection with the inspection and repair of the meniscus and ligaments of the knee and inspection and repair of the rotator cuff in the shoulder.

During arthroscopic surgery, multiple cannulas are typically inserted into the joint. One cannula accommodates the arthroscope through which the surgeon may visualize tissue and structures within the joint either directly or by projection of an image onto a monitor or screen. Additional operating cannulas allow the surgeon to approach the tissue within the joint from various angles with appropriate surgical instruments to perform a desired procedure.

In order to create greater visibility and working space, the joint typically is distended during arthroscopic surgery by providing a source of pressurized saline, such that the saline flows or is pumped into the joint to distend the joint and create working space. For example, a saline bag may be elevated to create a pressure head, with the outflow of the bag attached to the insufflation port of one or more of the arthroscopic cannulas. More commonly, a saline fluid pump issued to create a substantially constant fluid pressure. Saline fluid pressure of at least 40 millimeters of mercury is generally required to distend the joint sufficiently for arthroscopic surgery, and pressures of 70 to 80 millimeters of mercury are commonplace during arthroscopic surgery.

During arthroscopic surgery, the surgeon frequently manipulates the various cannulas to view different portions or structures within the joint or to manipulate, cut, remove, suture, staple, anchor or otherwise diagnose and repair conditions within the joint. Such manipulation of the various cannulas creates leverage against surrounding skin, fascia and muscle structures, thereby stretching and loosening such structures as the procedure progresses. During surgery a surgeon may also elect to change cannula diameter at a given entry site, removing a cannula of a first diameter and replacing it with a cannula of a different diameter to accommodate different size instrumentation. Such insertion and removal of the cannula can further contribute to opening of the incision and stretching and loosening of surrounding tissue. As the soft tissue surrounding the cannula stretches and loosens during arthroscopic surgery, pressurized saline within the joint penetrates various layers of tissue surrounding the joint and becomes dispersed through such tissues. The penetration of saline into surrounding soft tissues enlarges the soft tissue surrounding the joint and creates pressure on various tissues and vessels after surgery, prolonging discomfort and recovery time. A build up of saline fluid in the tissue layers surrounding the incision also makes the joint tense, making it difficult to manipulate the joint and instruments to desired angles during surgery. A further potential complication is migration of saline through tissue. By way of example only, if a patient is placed in a lateral position with the arm elevated during shoulder surgery, fluid penetrating tissue layers may migrate along the shoulder toward the neck, and may cause swelling around the neck including critical structures such as the windpipe. Presented with such a situation, a surgeon likely will elect to keep the patient for a longer post-operative period and may require an overnight stay for observation until the saline dissipates and concern about pressure on vital structures such as the windpipe, arteries or veins is reduced. In addition, loosening of soft tissue structures surrounding the arthroscopic cannula permits saline to leak from the joint capsule around the outside of the cannula. Leaking saline flows over the patient and onto the floor of the operating room, creating wet, slippery and undesirable operating conditions. Leakage of saline during arthroscopic surgery has become sufficiently commonplace that arthroscopic surgeons and operating room staff routinely wear waterproof boots in the operating room. In addition, suction equipment is routinely used to collect and remove puddles of leaked saline from the operating room floor. In addition to the inconvenience and safety issues created by puddles of saline, the loosening of tissue surrounding the cannula can also lead to expulsion of the cannula from the joint under the pressure of the saline. Expulsion of the cannula interrupts the procedure, prolonging surgery and exposure of the patient to anesthesia. If expelled with sufficient force, the cannula can also become a projectile, creating a safety hazard to the surgeon and operating room personnel. In addition, if an expelled cannula contacts a non-sterile surface, a replacement sterile cannula and a replacement instrument inserted through the cannula at the time of expulsion must be opened and re-inserted into the joint to continue surgery.

The loss of saline during surgery due to leakage between the cannula and the incision also increases the expense of the procedure as numerous bags of saline are used during the procedure in excess of the actual volume required to distend the joint during surgery. Due to such leakage, it is not uncommon to use three to six bags of saline, and over ten bags in extreme circumstances in an arthroscopic surgical procedure. Most of this saline leaks out of the joint or permeates tissue surrounding the joint. Each bag contains 3,000 cubic centimeters of saline, so several liters of saline may find its way into adjoining tissue or onto the operating room floor.

An arthroscopic cannula with an external thread is known. See for example Glowa U.S. Pat. No. 5,779,697.

Laparoscopic cannulas with anchors, including balloon structures to hold the cannula in place against accidental removal as instruments are inserted and removed, also are known. See for example Shichman U.S. Pat. No. 5,217,441; Yoon U.S. Pat. No. 5,445,615; Orth U.S. Pat. No. 5,836,913; and Hopper U.S. Pat. Nos. 5,697,946 and 6,524,283. The foregoing patents relate to abdominal, i.e., laparoscopic, surgery during which the abdomen is insufflated with carbon dioxide gas. Laparoscopic surgery utilizing gas insufflation does not implicate the considerations identified above with respect to leakage of saline during arthroscopic surgery.

SUMMARY OF THE DISCLOSURE

In accordance with the disclosure, an arthroscopic cannula is disclosed having an inflatable balloon associated therewith. The balloon preferably surrounds a portion of the cannula extending into the joint.

In use, the cannula is inserted into a human joint capsule to perform arthroscopic surgery. The balloon associated with the cannula is positioned to traverse the joint capsule wall. The balloon is inflated, such as by filling the balloon with saline, to secure the cannula to the surrounding soft tissue. The balloon tamps the tissue around the incision. This seals the opening surrounding the cannula to minimize and possibly prevent leakage of saline from the joint capsule, and seepage of saline into surrounding soft tissue which can lead to distension of the tissue and consequent discomfort and prolonged recovery.

In one embodiment, the balloon is mounted directly to the outer cannula wall and is inflated through a filling port and channel which are integral with the cannula and cannula housing, respectively. In an alternative embodiment, an adapter is provided with the balloon mounted to the adapter. The adapter has an open center lumen configured and dimensioned to receive an arthroscopic cannula. A typical arthroscopic cannula is inserted through the adapter and the combined arthroscopic cannula/adapter is inserted through an incision into the joint. The adapter is secured relative to the arthroscopic cannula and a balloon on the adapter is Mated to seal the incision and prevent dislodgement of the arthroscopic cannula.

It is considered important that the balloon transverse substantially the entire wall of the incision into the joint in order to form a seal with as many layers of tissue as possible and to spread the load of forces tending to eject the cannula from the body over as large a surface area as possible. The portion of the balloon extending into the inside of the joint, if any, should be minimized as there is insufficient space in the joint to allow the balloon to occupy precious operating space.

Thus, the device and method of performing arthroscopic surgery decrease leakage of saline between the incision and cannula, thereby decreasing saline use, minimizing distention of soft tissue surrounding the cannula and leakage of saline in the operating room.

The tamping pressure of the balloon on the tissue at the incision and the concomitant reduction in softening and distension of tissue surrounding the incision maintains the structural integrity of such tissue and makes it possible for the balloon to grip the tissue and securely hold the cannula in place in the incision during surgery. Advantageously, the balloon tamps and seals the tissue around the incision even if the cannula is manipulated during surgery or if cannulas are alternated and replaced during surgery. Thus, the sealing and tamping balloon of the present disclosure associated with an arthroscopic cannula substantially reduces or prevents leakage of saline around the cannula or into surrounding tissue during arthroscopic surgery, reducing tension in the joint during surgery and avoiding post operative complications due to migration of saline through tissue. Leakage of saline onto the patient and surrounding operating room floor is likewise minimized or eliminated.

BRIEF DESCRIPTION OF THE DRAWINGS

The accompanying drawings form a part of this disclosure, in which.

DETAILED DESCRIPTION OF THE PREFERRED EMBODIMENTS

Figure 1:
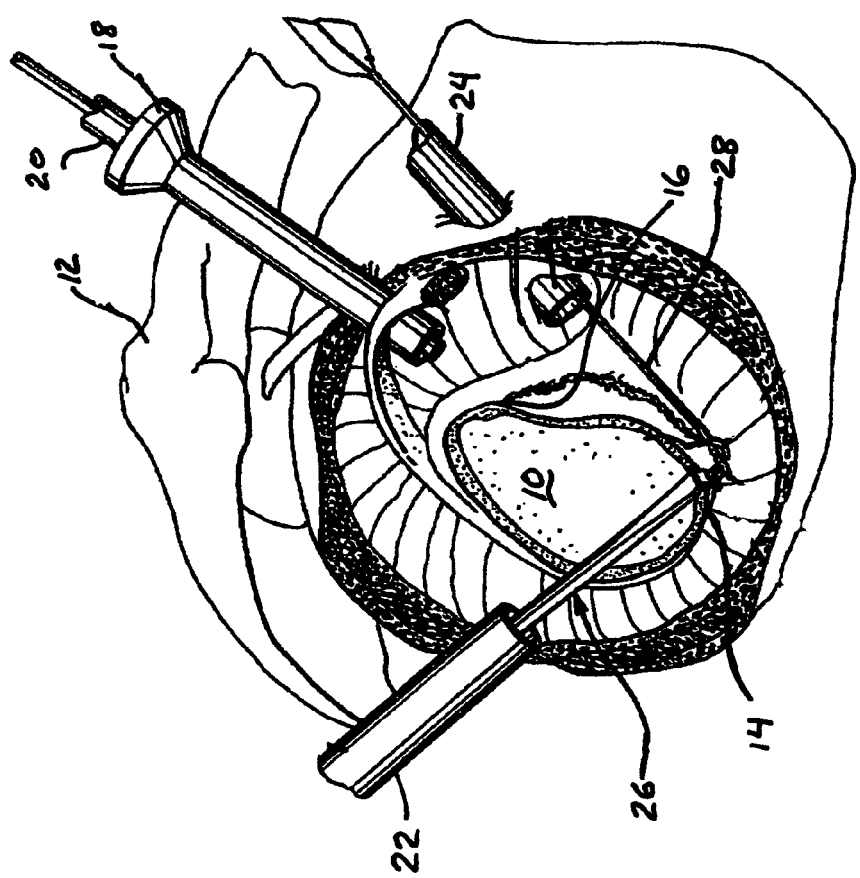
FIG. 1 is an illustration of a typical arthroscopic repair in the shoulder capsule.

FIG. 1 is a partial sectional illustration of a typical arthroscopic surgical repair. In FIG. 1, the shoulder joint is shown looking toward the glenoid cavity 10 with obstructing structures such as the humerous omitted. By way of providing a point of reference, the acromium is labeled 12. In the illustration of FIG. 1, a typical injury is illustrated in which the glenoid labrum has been torn from the anterior rim 14 and the inferior rim 16. A first cannula 18 has been inserted in a generally downward direction and an arthroscope 20 has been inserted at an appropriate orientation to view tissue within the joint capsule. Direct visualization through the arthroscope is possible, but more typically a camera is attached to the arthroscope and the image from the arthroscope is projected onto one or more monitors in the operating room. Auxiliary cannulas 22 and 24 have been inserted into the shoulder capsule and instruments 26 and 28 have been inserted to effect a surgical repair. FIG. 1 illustrates three typical, commercially available smooth walled cannulae traversing soft tissue structures, including skin, muscle and/or ligament tissue to access the joint capsule. Pressurized saline would enter the joint capsule to distend the joint through a fluid line attached to a fluid port on one or more of the cannulas.

Figure 2:
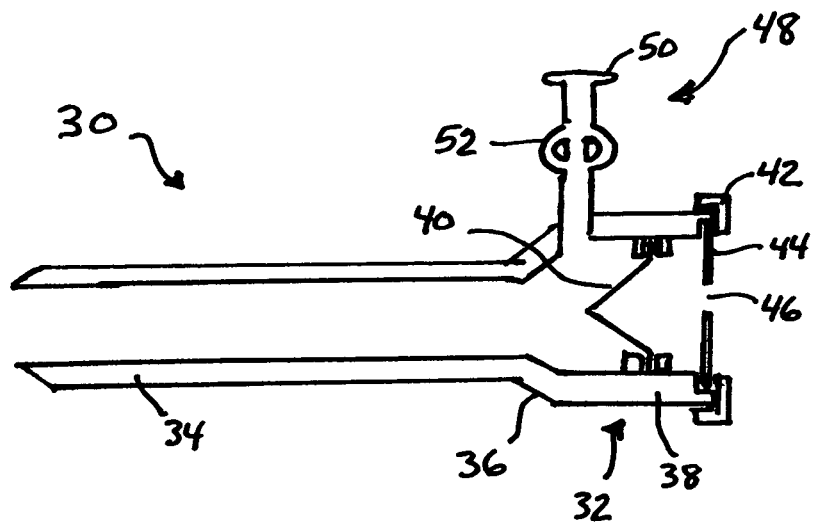
FIG. 2 is a cross-section view of a typical arthroscopic cannula.

Referring now to FIG. 2, a typical arthroscopic access cannula is shown in cross-section. Access cannula 30 includes a housing 32 with a cannula 34 extending therefrom. Cannula 34 typically has an internal diameter on the order of about 5 mm to 8 mm and a length sufficient to extend through soft tissue into the joint capsule to be operated on. A typical cannula length is on the order of about 30 cm. Housing 32 is generally wider than cannula 34 and has a tapered section 36 connecting cannula 34 to housing side wall 38. Housing 32 supports a zero seal 40 such as a duckbill valve as shown to seal against leakage when the cannula is inserted into the patient without any instrument inserted through the cannula. In addition, housing 32 supports a cap 42 which holds a secondary seal 44 in place across the open top of the cannula housing. Secondary seal 44 is a flat elastomeric septum with an opening 46 in the center thereof to receive an instrument inserted through the cannula apparatus. Opening 46 is on the order of about 2 mm to 4 mm to facilitate insertion of a surgical instrument into the access cannula. Secondary seal 44 forms a seal with a surgical instrument inserted into the cannula but does not seal the access cannula when no instrument is inserted. Thus, without an instrument inserted into the cannula, zero seal 40 forms a seal to prevent leakage through the cannula. When a surgical instrument such as an arthroscope, suturing device, needle passer, grasper, scissor, or the like is inserted through the cannula, zero seal 40 does not form a complete seal around the instrument shaft. Rather, secondary seal 44 forms a seal around the instrument shaft. Housing 32 also supports a fluid port 48 having a flanged or open end 50 to be attached to a saline fluid port, and stopcock valve 52 that may be opened (as shown in cross section in FIG. 2) to allow introduction of fluid into the joint cavity to distend the joint, or alternatively closed to seal against leakage of fluid from the joint. By way of example, one port might be connected to a source of saline with the stopcock open to permit inflow of saline into the joint, with another access cannula disposed extending into the joint not connected to a source of saline and having the stopcock in the closed position to prevent egress of saline. Of course, if during surgery it is necessary or desirable to change the access port to which saline is provided, the saline source is merely changed to another access port by closing the stopcock to which the saline is connected, disconnecting the source of saline, connecting the saline to a second access cannula stopcock valve, and opening the second cannula stopcock valve.

In accordance with the present disclosure, an arthroscopic cannula is provided with an expandable balloon structure surrounding at least a portion of the cannula portion of the arthroscopic cannula. The cannula with the surrounding balloon in a deflated condition is inserted through soft tissue into the joint capsule in a customary manner, and the balloon is inflated to seal the opening through the soft tissue and prevent pressurized saline introduced into the joint from penetrating into the adjacent soft tissue, such as between the various tissue layers, and also from leaking out of the incision around the arthroscopic cannula, particularly as the cannula is manipulated in the soft tissue during surgery.

Figure 3:
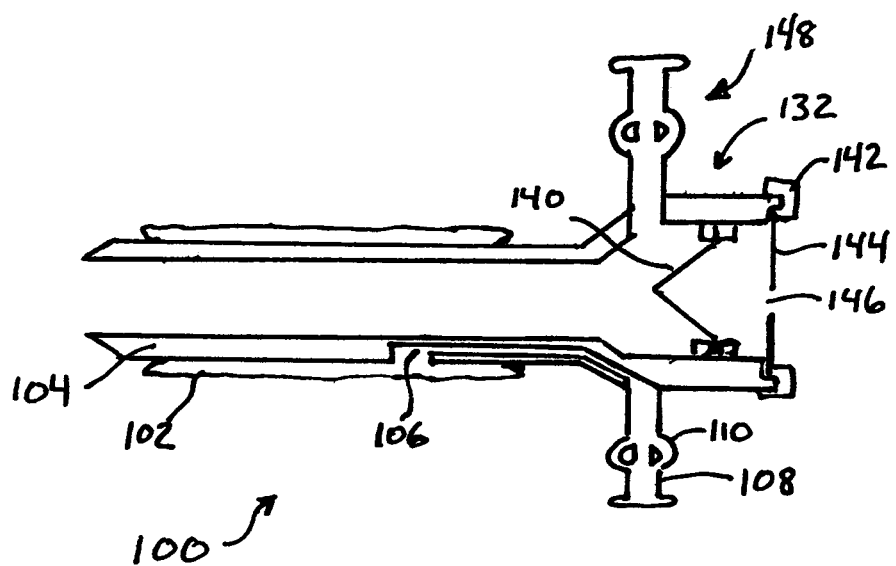
FIG. 3 is a cross-section view of an arthroscopic cannula in accordance with a first embodiment illustrating a balloon mounted to the arthroscopic cannula with an integral filling port and channel.

Referring now to FIG. 3, an arthroscopic cannula 100 is shown in cross-section having a balloon 102 mounted to and extending along at least a portion of the cannula 104. As shown, balloon 102 is attached to the exterior wall of cannula 104, such as by gluing, welding or the like. A balloon filling channel 106 with an associated filling port 108 allows the user to fill the balloon to the desired pressure, as described below. Filling port 108 has a stopcock valve 110 to open and close access to filling channel 106. In FIG. 3 filling channel 106 is shown integrally formed into a portion of the cannula side wall. While this configuration is preferred, it is also contemplated that the filling channel also could comprise a conduit such as a fine diameter hose extending directly from the balloon to a filling port, and not attached to or integrated into the cannula. Optionally, such a hose could be adhered to the outside wall of the cannula and have a filling port at the end thereof. Introducing fluid (which may be liquid or gas) through the filling port and channel into the balloon inflates the balloon. See FIGS. 5-6 for one example of such a hose and stopcock arrangement. As shown in FIG. 3, arthroscopic cannula 100 also includes a duckbill "zero" seal 140, a secondary seal 144 with an open center 146, a cap 142 securing secondary seal 144 to housing 132, and an insufflation port 148.

Figure 4A:
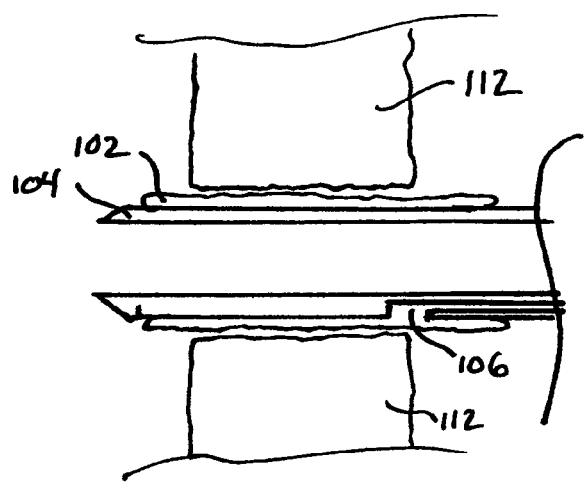
FIGS. 4A and 4B are partial cross-section schematic views illustrating the cannula of FIG. 3 inserted through an incision into a joint, with the balloon in an uninflated and inflated state, respectively.
Figure 4B:
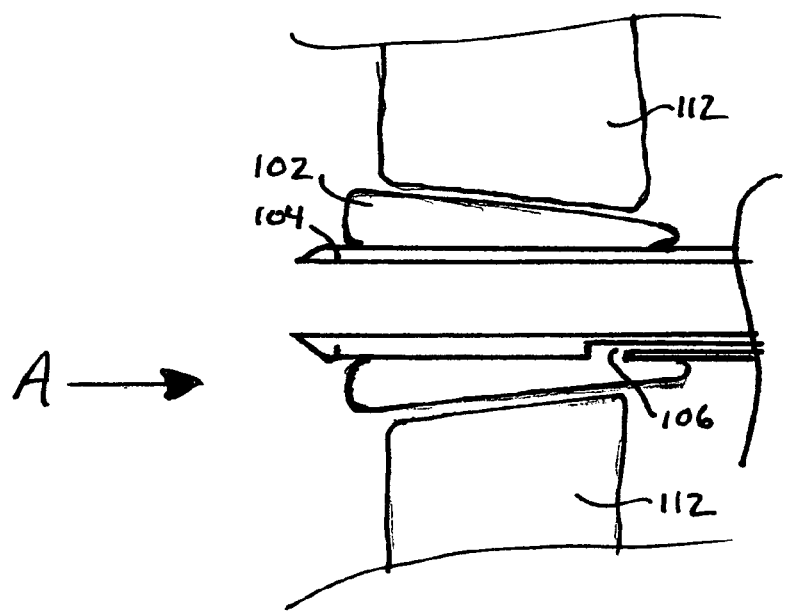

In use, the surgeon prepares the entry site in accordance with usual practice and inserts the cannula 104 with balloon 102 mounted thereon through soft tissue 112 that surrounds the joint capsule until the tip of the cannula enters the joint capsule. FIG. 4A illustrates cannula 104 inserted through soft tissue 100 prior to inflation of the balloon. The surgeon then inflates the balloon, such as by attaching a saline filled syringe to filling port 108 with stopcock valve 112 in the open position, and injecting saline into balloon 102 until the desired pressure is achieved. Stopcock valve 108 is then closed to maintain inflation of the balloon. Optionally, the syringe may then be removed so as not to obstruct the surgical field. As shown in FIG. 4B, inflated balloon 102 exerts a tamping pressure against the surrounding soft tissue 112, effectively sealing the soft tissue against the penetration of pressurized saline into or between tissue layers, and also sealing the incision through the soft tissue 112 to reduce and possibly prevent fluid leakage from the joint capsule around the cannula. With the joint filled with saline and distended for arthroscopic surgery, saline fluid pressure exerts pressure against the cannula in the direction of arrow "A". As shown, balloon 102 preferably is configured to have a larger diameter adjacent the open end of the cannula so as to create a wedging action when the cannula is subjected to the pressure of fluid used to fill and distend the joint capsule during surgery. While such a tapered balloon is desirable, tests with a substantially cylindrical shaped balloon have achieved the desired sealing of the incision and securing of the cannula in place. The space available to the surgeon within the filled joint capsule is very limited, and it is important that the balloon not occupy any substantial space inside the joint capsule. Thus, it is preferred that the balloon traverse and inflate along the walls of the soft tissue 112 that define the incision entry opening without occupying any substantial space on the inside of the joint. Preferably, the balloon does not extend more than a few millimeters into the joint. Additional cannulas with sealing balloons may be placed into the joint at multiple locations in order to provide multi-port access to the joint, with the sealing balloons on each cannula inflated to secure each cannula in place and seal the incision surrounding the cannula. Surgery is performed in a customary manner, with the balloon on each cannula holding the cannula in place and sealing the incision around the cannula against saline leakage as instruments are inserted and manipulated during surgery.

Figure 5:
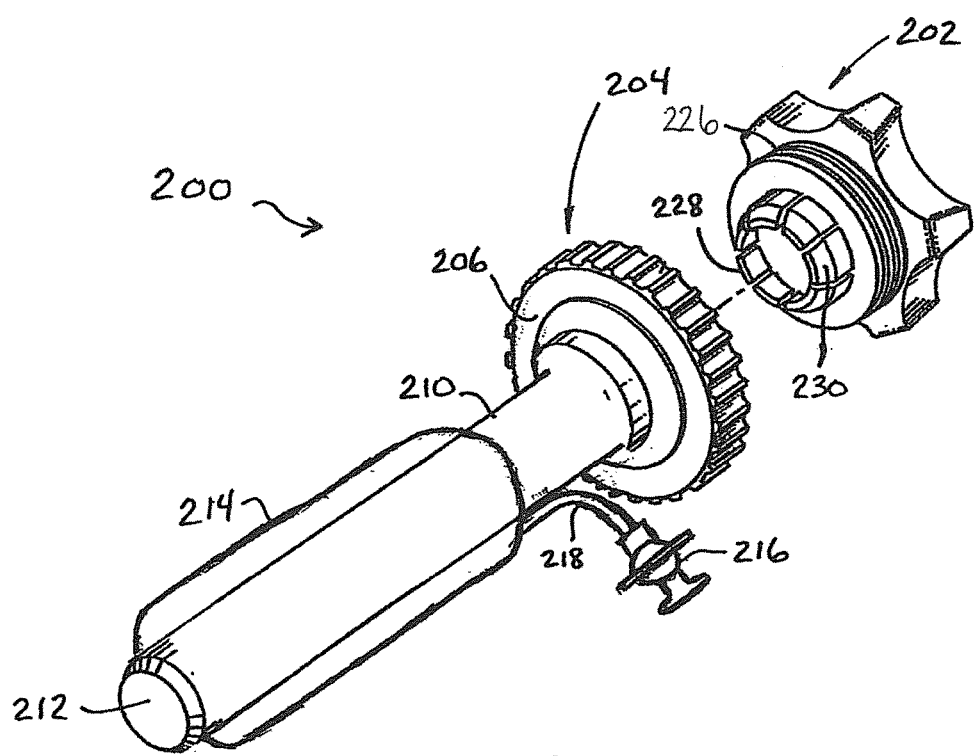
FIG. 5 is a perspective view, with parts separated, of an arthroscopic cannula adapter in accordance with a second embodiment.
Figure 6:
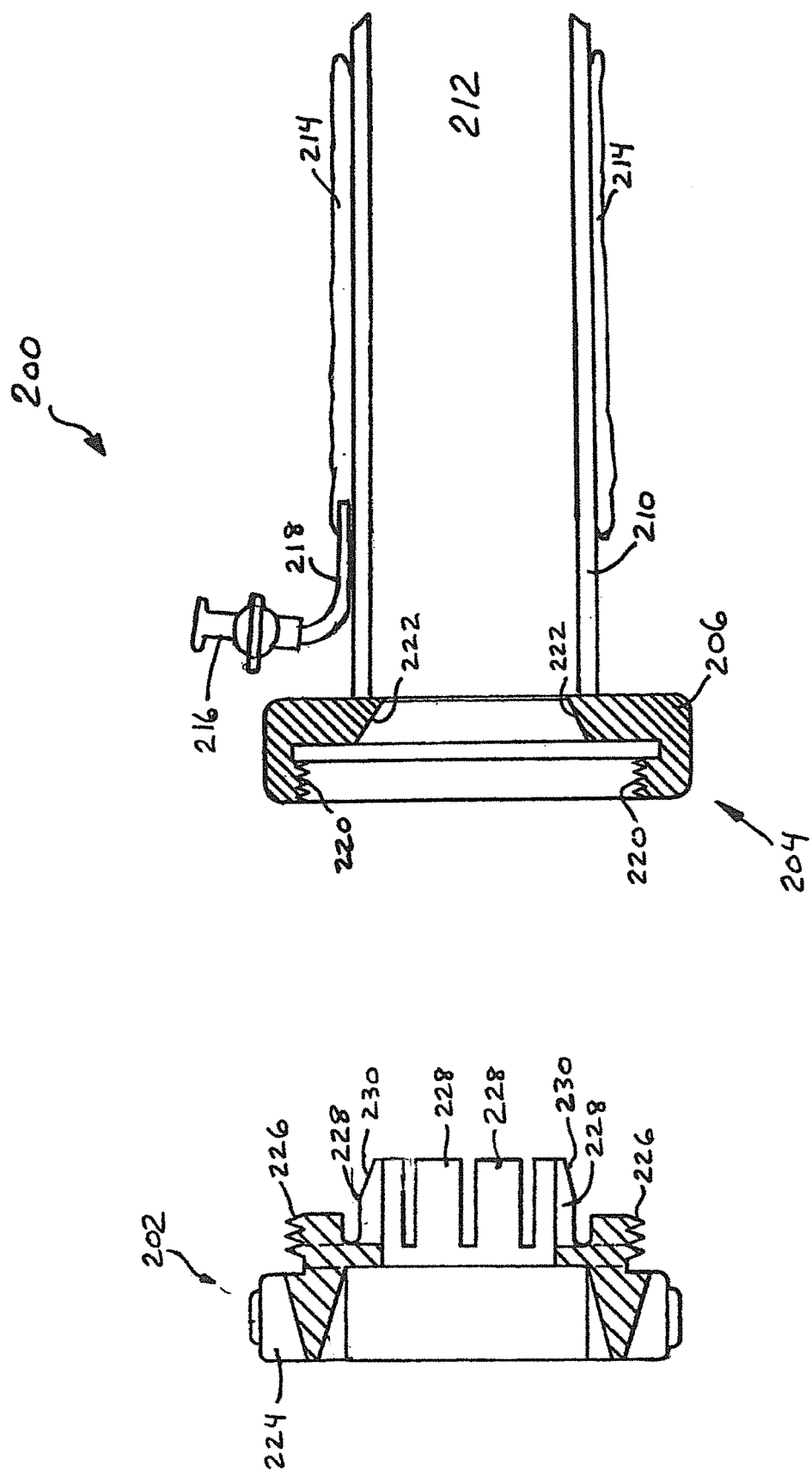
FIG. 6 is a cross-section view of the adapter of FIG. 5.

In the foregoing embodiment, it is contemplated that the balloon will be mounted directly to the cannula. Alternative embodiments are contemplated in which the sealing balloon is part of an adapter that can be mounted over a traditional cannula. One configuration of a sealing adapter that may be mounted over a traditional arthroscopic cannula is shown in FIGS. 5 and 6. FIG. 5 is a perspective view with parts separated of an arthroscopic cannula adapter 200 having a collet portion 202 and a sleeve portion 204. The sleeve portion has a sleeve handle section 206 configured to be gripped by the user and adapted to threadingly engage collet portion 202, as will be explained in greater detail below. Sleeve 210 extends from sleeve handle section 206 and has an open center lumen 212 configured and dimensioned to receive and slide over the cannula of a standard arthroscopic cannula such as the cannula shown in FIG. 2. Sleeve 210 has balloon 214 mounted thereon, such as by gluing welding or the like. A filling port 216 is provided which communicates through a filling hose 218 with the interior of balloon 214 in order to fill the balloon during use. Of course, the hose and stopcock arrangement shown in FIGS. 5-6 is merely one possible embodiment. It is also contemplated that the fluid filling channel and port may be integrated into the cannula adapter in a manner similar to the embodiment shown in FIGS. 3 and 4A-4B.

FIG. 6 is a cross-section view of the adapter of FIG. 5 with parts separated. As shown, adapter 200 has a sleeve 210 and a handle 206 with an open center 212 extending through the handle portion and the sleeve. A balloon 214 is mounted around sleeve 210 and is in fluid communication with a filling port 216, such as via channel 218, for filling of the balloon. Handle 206 has internal threads 220 and tapered inner wall 222. Collet portion 202 has an open center aligned with open center 212, a collet grip portion 224, externally threaded section 226 and collet fingers 228, each having a tapered tip 230. External threads 226 are configured to threadingly engage internal threads 220 of handle 206, so that as collet portion 202 is threadingly mated to handle 206, the tapered tips 230 of fingers 228 engage tapered wall 222. In this manner, fingers 228 are cammed radially inwardly as the handle and collet sections are tightened together.

In use, adapter 200 is assembled with collet portion 202 loosely engaged with handle 206, i.e., with threads 226, 220 engaged but not tightened. A typical arthroscopic cannula is inserted through the open center of the collet and through the open center 212 of sleeve 210 to a desired position, such as with the tip of the arthroscopic cannula adjacent the tip of sleeve 210. Collet 208 is then rotated to tighten the collet portion to handle 206, bringing tapered tips 230 of collet fingers 228 into engagement with inner tapered wall 222. As a result of the camming action of inner wall 222 on tapered tips 230, fingers 228 are compressed radially inward to grip and hold the arthroscopic cannula inserted therethrough, thereby holding the arthroscopic cannula relative to the adapter.

The combined arthroscopic cannula and adapter apparatus is then inserted through an incision in soft tissue so that the cannula adapter sleeve balloon traverses the soft tissue layers of the incision into the joint capsule in a manner similar to FIG. 4A. With the cannula/adapter combination inserted into the joint and the adapter secured to the cannula, the balloon is inflated through inflation port 216 as previously described to securely hold the combined arthroscopic cannula/adapter in place and seal the incision around the cannula against fluid leakage and penetration of saline into surrounding layers of soft tissue, resulting in an expanded balloon tamping soft tissue in a manner similar to that shown in FIG. 4B.

It also contemplated that the combined arthroscopic cannula and adapter may be inserted into the incision with the adapter loosely mounted over the arthroscopic cannula. In this manner, the arthroscopic cannula and adapter may be inserted into the joint and adjusted relative to each other and the patient until the desired position is achieved. Once the arthroscopic cannula and adapter are respectively located as desired relative to each other and tissue the adapter may be secured relative to the arthroscopic cannula, and the balloon inflated to seal the incision and anchor the cannula.

As will be appreciated, the collet configuration is just one way to secure the adapter to the arthroscopic cannula, and many other arrangements to secure a balloon adapter to an arthroscopic cannula are possible. For example, an arthroscopic cannula may be provided with a bayonet style engagement to engage a corresponding engagement structure on the adapter. As a further alternative, a camming structure that effectively reduces the diameter of the opening through the center of the adapter to grip the cannula inserted therethrough may be provided. For example, an over-center cam which effectively reduces the inner diameter of the adapter to grip the cannula also is contemplated to secure the adapter to the arthroscopic cannula. By way of analogy, such a structure would grip the cannula in much the same manner as tightening a belt. Alternatively, the adapter sleeve may have a thin flexible layer along all or part of its length so that inflation of the balloon simultaneously exerts an inward force to grip the arthroscopic cannula as it also exerts a radially outward force to tamp the soft tissue surrounding the cannula to anchor the cannula and seal the incision and tissue layers.

The foregoing disclosure contains many specifics relating to preferred embodiments. However, many variations will occur to those skilled in the art empowered by knowledge of the foregoing disclosure, and therefore the claims of the present application should not be construed as limited to the foregoing specific embodiments.

What is claimed is:

1. A method of performing arthroscopic surgery comprising:
    providing an arthroscopic cannula having an arthroscopic cannula housing supporting a seal and an arthroscopic cannula extending therefrom;
    providing a balloon adapter having an adapter housing with an opening therethrough and an adapter cannula extending therefrom and a balloon mounted to the outer surface of the adapter cannula;
    inserting the arthroscopic cannula through the adapter housing opening and into the adapter cannula to form an arthroscopic cannula and adapter assembly;
    inserting the arthroscopic cannula and adapter assembly into a joint with the balloon traversing substantially the entire wall of the incision;
    inflating the balloon to form a seal between the cannula and adapter assembly and surrounding tissue
    distending the joint by introducing pressurized saline into the joint;
    performing arthroscopic surgery through the arthroscopic cannula with the cannula positioned in the adapter and with the joint distended by the pressurized saline.

2. The method of claim 1 wherein said step of inserting the arthroscopic cannula further comprises securing the adapter housing to the cannula housing.

3. The method of claim 1 further comprising the steps of:
    deflating the balloon;
    removing the cannula from the joint;
    closing the cannula entry.

* * * * *